US010557157B2

(12) United States Patent
Noordam

(10) Patent No.: US 10,557,157 B2
(45) Date of Patent: Feb. 11, 2020

(54) PROCESS FOR ENZYMATIC HYDROLYSIS OF LIGNOCELLULOSIC MATERIAL AND FERMENTATION OF SUGARS

(71) Applicant: DSM IP ASSETS B.V., Heerlen (NL)

(72) Inventor: Bertus Noordam, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 13 days.

(21) Appl. No.: 15/535,809

(22) PCT Filed: Dec. 16, 2015

(86) PCT No.: PCT/EP2015/079973
§ 371 (c)(1),
(2) Date: Jun. 14, 2017

(87) PCT Pub. No.: WO2016/096971
PCT Pub. Date: Jun. 23, 2016

(65) Prior Publication Data
US 2017/0369917 A1    Dec. 28, 2017

(30) Foreign Application Priority Data

Dec. 19, 2014    (EP) .................................... 14199262

(51) Int. Cl.
| C12P 19/14 | (2006.01) |
| C12P 7/10  | (2006.01) |
| C12P 7/14  | (2006.01) |
| C12P 19/02 | (2006.01) |
| C12N 9/30  | (2006.01) |

(52) U.S. Cl.
CPC .............. *C12P 19/14* (2013.01); *C12N 9/242* (2013.01); *C12P 7/10* (2013.01); *C12P 7/14* (2013.01); *C12P 19/02* (2013.01); *C12P 2201/00* (2013.01)

(58) Field of Classification Search
CPC .... C12P 19/14; C12P 7/14; C12P 7/10; C12P 2201/00; C12N 9/242; Y02E 50/16; Y02E 50/17
See application file for complete search history.

(56) References Cited

U.S. PATENT DOCUMENTS

| 9,957,528 B2 | 5/2018 | Noordam et al. |
| 9,982,280 B2 | 5/2018 | Noordam et al. |
| 10,087,475 B2 | 10/2018 | Noordam et al. |
| 10,144,939 B2 | 12/2018 | Noordam et al. |
| 2009/0035826 A1 | 2/2009 | Tolan et al. |
| 2010/0159535 A1 | 6/2010 | Xu et al. |
| 2010/0304437 A1 | 12/2010 | Garner et al. |
| 2010/0330633 A1 | 12/2010 | Walther et al. |
| 2012/0114797 A1 | 5/2012 | Perkins et al. |
| 2012/0183993 A1 | 7/2012 | Smits et al. |
| 2014/0186912 A1 | 7/2014 | Trupia |
| 2015/0007903 A1 | 10/2015 | Noordam et al. |
| 2015/0299749 A1 | 10/2015 | Noordam et al. |
| 2015/0315622 A1 | 11/2015 | Frickmann et al. |
| 2019/0093137 A1 | 3/2019 | Smits et al. |

FOREIGN PATENT DOCUMENTS

| CN | 102325889 A | 1/2012 |
| CN | 102459582 A | 5/2012 |
| CN | 103314111 A | 9/2013 |
| EP | 0058426 A1 | 8/1982 |
| JP | 2008/521396 A | 6/2008 |
| JP | 2010/531668 A | 9/2010 |
| JP | 2012/504937 A | 3/2012 |
| WO | 94/03634 A1 | 2/1994 |
| WO | 01/60752 A1 | 8/2001 |
| WO | 2006/056838 A1 | 6/2006 |
| WO | 2007/091231 A1 | 8/2007 |
| WO | 2008/008793 A2 | 1/2008 |
| WO | 2009/003167 A1 | 12/2008 |
| WO | 2009/046538 A1 | 4/2009 |
| WO | 2009/055793 A1 | 4/2009 |
| WO | 2010/138754 A1 | 2/2010 |
| WO | 2010/080407 A2 | 7/2010 |
| WO | 2011/000949 A1 | 1/2011 |
| WO | 2011/042437 A3 | 4/2011 |
| WO | 2012019151 A1 | 2/2012 |
| WO | 2012/061517 A1 | 5/2012 |
| WO | 2012/088429 A2 | 6/2012 |
| WO | 2012/149275 A1 | 11/2012 |
| WO | 2013/028701 A1 | 2/2013 |
| WO | 2014/072392 A1 | 5/2014 |
| WO | 2014/072393 A1 | 5/2014 |
| WO | 2014072392 A1 | 5/2014 |
| WO | 2014072393 A1 | 5/2014 |
| WO | 2014130812 A1 | 8/2014 |
| WO | 2015/075277 A1 | 5/2015 |

OTHER PUBLICATIONS

Cannella et al., Biotechnol. Bioeng., 2014, vol. 111, p. 59-68, and 3 pages of Supplementary Information, first published online on Sep. 11, 2013 in Wiley Online Library.*
Tomas-Pejo et al., Biotechnol. Bioeng., 2008, vol. 100, p. 1122-1131.*
Schell et al., Applied Biochemistry and Biotechnology, 1990, vol. 24/25 p. 287-297.*
bioz.com, "Celluclast 1.5 L" product Overview, downloaded on Dec. 20, 2018, 3 pages of PDF.*
Merriam-Webster, definition of "headspace" downloaded on Dec. 20, 2018.*
International Search Report of International Patent Application No. PCT/EP2013/073250 dated Jan. 8, 2014.
Bey et al., "Cello-oligosaccharide oxidation reveals differences between two lytic polysaccharide monooxygenases (family GH61) from Podospora anserina", Applied and Environmental Microbiology, vol. 79, Nov. 2, 2012 (Nov. 2, 2012), pp. 488-496, XP008160285.
Kostylev et al., "Synergistic Interactions in Cellulose Hydrolysis", Biofuels, vol. 3, Jan. 2012 (Jan. 2012), pp. 61-70, XP002693861.

(Continued)

*Primary Examiner* — Kade Ariani
(74) *Attorney, Agent, or Firm* — McBee Moore & Vanik IP, LLC

(57) ABSTRACT

The invention relates to a process for the preparation of a sugar and/or fermentation product from lignocellulosic material.

16 Claims, No Drawings

(56) References Cited

OTHER PUBLICATIONS

Horn et al., "Novel Enzymes for the Degradation of Cellulose", Biotechnology for Biofuels, vol. 5, Jul. 2, 2012 (Jul. 2, 2012), pp. 45(1)-56 (12), XP021122735.
Viikari et al., "Lignocellulosic ethanol: From science to industry", Elsevier, SciVerse ScienceDirect,' Biomass and Bioenergy 46 (2012) pp. 13-24, XP-002718612.
Deng et al., "Influence of culture aeration on the cellulase activity of Thermobifida fusca", Appl Microbial Biotechnol (2010), Biotechnological Products and Process Engineering, pp. 965-974, XP19778511.
Hu et al., "The synergistic action of accessory enzymes enhances the hydrolytic potential of a "cellulase mixture" but is highly sustrate specific", Biotechnology for Biofuels 2013, 6:112, XP21158122A; pp. 1-12.
Kumar et al., "Recent Advances in Production of Bioethanol from Lignocellulosic Biomass." Chem. Eng. Technol. (2009) 32(4) 517-526.
Badger, "Ethanol From Cellulose: A General Review." Reprinted from: Trends in new crops and new uses. 2002.
Cannella et al., "Production and effect of aldonic acids during enzymatic hydrolysis of lignocellulose at high dry matter content." Biotechnology for Biofuels 2012, 5:26.
Cannella et al., "Do New Cellulolytic Enzyme Preparations Affect the Industrial Strategies for High Solids Lignocellulosic Ethanol Production?" XP-002721360. Biotechnology and Bioengineering 2014, 111:1.
Levasseur et al., "Expansion of the enzymatic repertoire of the CAZy database to integrate auxiliary redox enzymes." Biotechnology for Biofuels 2013, 6:41.
Ioelovich et al., "Study of Enzymatic Hydrolysis of Pretreated Biomass at Increased Solids Loading." Bio Resources (2012), 7(4), 4672-4682.
Sweeney, Matt D. et al., "Biomass Converting Enzymes as Industrial Biocatalysts for Fuels and Chemicals: Recent Developments", Catalysts, Apr. 12, 2012, pp. 244-263.
Quinlan, R. Jason et al., "Insights into the Oxidative Degradation of Cellulose by a Copper Metalloenzyme that Exploits Biomass Components", PNAS, Sep. 13, 2011, pp. 15079-15084, vol. 108, No. 37.
Phillips et al., "Cellobiose Dehydrogenase and a Copper-Dependent Polysaccharide Monooxygenase Potentiate Cellulose Degradation by Neurospora crassa" American Chemical Society Chemical Biology, vol. 6, No. 12, pp. 1399-1406 (and supplement) electronically published Oct. 17, 2011.
International Search Report of International Patent Application No. PCT/EP2013/073255 dated Jan. 23, 2014.
International Search Report of International Patent Application No. PCT/EP2013/073253 dated Mar. 21, 2014.
International Search Report of International Patent Application No. PCT/EP2015/059317 dated Jul. 20, 2015.
International Search Report of International Patent Application No. PCT/EP2015/051839 dated Apr. 28, 2015.
Podkaminer, Kara K et al., "Ethanol and Anaerobic Conditions Reversibly Inhibit Commercial Cellulase Activity in Thermophilic Simultaneous Saccharification and Fermentation (tSSF)", Biotechnology for Biofuels, Jun. 15, 2012, vol. 5, No. 1, Biomed Central Ltd, GB.
Kumar, Manoj, "Development of a commercial enzyme system for lignocellulosic biomass saccharification", Final Technical Report, DSM Innovation Inc., 2012, pp. 1-23, DE-FC608GO18079.

\* cited by examiner

US 10,557,157 B2

PROCESS FOR ENZYMATIC HYDROLYSIS OF LIGNOCELLULOSIC MATERIAL AND FERMENTATION OF SUGARS

CROSS-REFERENCE TO RELATED APPLICATIONS

This application is a National Stage entry of International Application No. PCT/EP2015/079973 filed 16 Dec. 2015, which claims priority to European Patent Application No. 14199262.8, filed 19 Dec. 2014.

FIELD OF THE INVENTION

The invention relates to a process for the enzymatic hydrolysis of lignocellulosic material and fermentation of sugars.

BACKGROUND OF THE INVENTION

Lignocellulosic material is primarily composed of cellulose, hemicellulose and lignin and provides an attractive platform for generating alternative energy sources to fossil fuels. The material is available in large amounts and can be converted into valuable products e.g. sugars or biofuel, such as bioethanol.

Producing fermentation products from lignocellulosic material is known in the art and generally includes the steps of pretreatment, hydrolysis, fermentation, and optionally recovery of the fermentation products.

During the hydrolysis, which may comprise the steps of liquefaction, pre-saccharification and/or saccharification, cellulose present in the lignocellulosic material is partly (typically 30 to 95%, dependable on enzyme activity and hydrolysis conditions) converted into reducing sugars by cellulolytic enzymes. The hydrolysis typically takes place during a process lasting 6 to 168 hours (see Kumar, S., Chem. Eng. Technol. 32 (2009), 517-526) under elevated temperatures of 45 to 50° C. and non-sterile conditions.

Commonly, the sugars are then converted into valuable fermentation products such as ethanol by microorganisms like yeast. The fermentation takes place in a separate, preferably anaerobic, process step, either in the same or in a different vessel. The temperature during fermentation is adjusted to 30 to 33° C. to accommodate growth and ethanol production by microorganisms, commonly yeasts. During the fermentation process, the remaining cellulosic material is converted into reducing sugars by the enzymes already present from the hydrolysis step, while microbial biomass and ethanol are produced. The fermentation is finished once the cellulosic material is converted into fermentable sugars and all fermentable sugars are converted into ethanol, carbon dioxide and microbial biomass. This may take up to 6 days. In general, the overall process time of hydrolysis and fermentation may amount up to 13 days.

In general, cost of enzyme production is a major cost factor in the overall production process of fermentation products from lignocellulosic material (see Kumar, S., Chem. Eng. Technol. 32 (2009), 517-526). Thus far, reduction of enzyme production costs is achieved by applying enzyme products from a single or from multiple microbial sources (see WO 2008/008793) with broader and/or higher (specific) hydrolytic activity. This leads to a lower enzyme need, faster conversion rates and/or a higher conversion yields, and thus to lower overall production costs.

Next to the optimization of enzymes, optimization of process design is a crucial tool to reduce overall costs of the production of fermentation products.

For economic reasons, it is therefore desirable to include new and innovative process configurations aimed at reducing overall production costs in the process involving hydrolysis and fermentation of lignocellulosic material.

SUMMARY OF THE INVENTION

An object of the invention is to provide an improved process for the preparation of a sugar product and/or a fermentation product from lignocellulosic material. Another object is to provide a process involving hydrolysis, wherein the process conditions of the hydrolysis are optimized. Optimization lies in any of the following features.

The hydrolysis process performed in the present invention comprises at least two steps, a step wherein the enzymatic hydrolysis is performed at a first temperature and a second step wherein the enzymatic hydrolysis is performed at a second temperature, wherein the second temperature is lower than the first temperature. Oxygen is added to the hydrolysis during at least part of the second step.

Oxygen not only stimulates glucan hydrolysis, it also leads to enzyme inactivation. This inactivation can be limited by application of oxygen at lower temperature. The application of oxygen at low temperature does not have a negative effect on the glucan hydrolysis. It is therefore beneficial to apply oxygen (aeration) at a lower temperature than the optimal enzyme performance temperature.

A very accurate and careful oxygen addition and control is essential in case oxygen is applied at the optimal enzyme performance temperature (maximal enzyme performance at the lowest possible enzyme inactivation). This is difficult and more expensive compared with oxygen addition at decreased temperature, since at low temperature there is a limited, or even absent, enzyme inactivation. Therefore, oxygen addition at decreased temperature allows for cheap and easy controllable oxygen addition.

Large scale ethanol production facilities normally contain several lignocellulosic feedstock hydrolysis containers (that often operate in parallel) and also several fermentation containers in which ethanol is produced. To reduce cost, large scale ethanol production facilities generally contain only one heat exchanger to cool the biomass after hydrolysis to a suitable fermentation temperature. If oxygen addition is applied after the heat exchanger and prior to fermentation, only one oxygen addition system is needed. This solution is much cheaper than when oxygen is added to each individual hydrolysis container.

Oxygen addition at low temperature (e.g. fermentation temperature) can be combined with yeast propagation prior to the ethanol fermentation process. So, the propagation step wherein yeast is propagated can be combined with the second stage of the processes according to the present invention.

Oxygen addition at reduced temperature leads to reduced lignin oxidation and consequently a reduced pH drop. The necessity for pH control might therefore be absent.

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

In case liquefaction and saccharification are combined, the one or more containers used in the first stage are called first container(s), the one or more containers used in the second stage are called second container(s) and the one or more containers used in the fermentation are called third container(s). In case liquefaction and saccharification are separate steps, the one or more containers used for the liquefaction are called first container(s), the one or more containers used in the saccharification are called second container(s), the one or more containers used in the second stage are called third container(s) and the one or more containers used in the fermentation are called fourth container(s).

The container used in the second stage can be a container, but can also be a tube or any other continuous system. The second stage may also be performed in the one or more fermentation containers before the fermentation starts. Oxygen may be introduced through sparging, but may also be introduced by filling the one or more containers from the top, allowing the hydrolysate to fall down and consequently introduce sufficient oxygen into the hydrolysate. In an embodiment oxygen is added before the fermenting microorganism is added. The second stage may also be performed in the one or more containers used for the propagation of the fermenting microorganisms (propagation containers). Oxygen may be introduced through sparging, but may also be introduced by filling the one or more propagation containers from the top, allowing the hydrolysate to fall down and consequently introduce sufficient oxygen into the hydrolysate.

The present invention relates to a process for the preparation of a sugar product from lignocellulosic material, comprising the step of enzymatic hydrolysis of the lignocellulosic material in one or more containers using an enzyme composition comprising at least two cellulases to obtain a sugar product, wherein the enzymatic hydrolysis comprises at least a first stage wherein the enzymatic hydrolysis is performed at a first temperature, and a second stage wherein the enzymatic hydrolysis is performed at a second temperature, wherein the second temperature is lower than the first temperature and wherein oxygen is added to the hydrolysis during at least part of the second stage.

The present invention also relates to a process for the preparation of a fermentation product from lignocellulosic material, comprising the following steps (a) performing a process for the preparation of a sugar product from lignocellulosic material as described above, (b) fermentation of the sugar product to produce a fermentation product, and (c) optionally, recovery of the fermentation product.

In an embodiment the processes of the present invention comprise a first stage wherein the enzymatic hydrolysis is performed at a first temperature. Said first temperature is from 50-90° C., preferably from 52-80° C., more preferably from 55-75° C. and most preferably from 57-65° C.

The first stage of the processes according to the present invention may be an enzymatic hydrolysis wherein liquefaction and saccharification are combined. In an embodiment the first stage is anaerobic. Alternatively, the first stage of the processes according to the present invention may be an enzymatic hydrolysis wherein liquefaction and saccharification are separate steps. Liquefaction and saccharification may be performed at different temperatures, but may also be performed at a single temperature, such as the first temperature described above. In an embodiment the temperature of the liquefaction is higher than the temperature of the saccharification. Liquefaction is preferably carried out at a temperature of 65-75° C. and saccharification is preferably carried out at a temperature of 50-65° C.

The present invention also relates to a process for the preparation of a sugar product from lignocellulosic material, comprising the step of enzymatic hydrolysis of the lignocellulosic material in one or more containers using an enzyme composition comprising at least two cellulases to obtain a sugar product, wherein the enzymatic hydrolysis comprises at least (a) a first stage, said first stage comprising a liquefaction step and a saccharification step, wherein the liquefaction step is performed at a first temperature and the saccharification step is performed at a second temperature, wherein the second temperature is lower than the first temperature, and (b) a second stage wherein the enzymatic hydrolysis is performed at a third temperature, wherein the third temperature is lower than the second temperature and wherein oxygen is added to the hydrolysis during at least part of the second stage. In an embodiment the first stage is performed in one or more first containers. In an embodiment the second stage is performed in one or more second containers. When liquefaction and saccharification are separate steps, the liquefaction step may be performed in one or more first containers and the saccharification step may be performed in one or more second containers and the second stage may be performed in one or more third containers.

In an embodiment the processes of the present invention comprise a second stage wherein the enzymatic hydrolysis is performed at a second temperature. Said second temperature is from 20-49° C., preferably 25-45° C., more preferably 30-40° C. In case of a process wherein liquefaction and saccharification are separate steps, the temperature of the second stage is called third temperature. In such cases, the processes of the present invention comprise a second stage wherein the enzymatic hydrolysis is performed at a third temperature. Said third temperature is from 20-49° C., preferably 25-45° C., more preferably 30-40° C.

In the processes according to the present invention lignocellulosic material may be added to the one or more first containers. In an embodiment the enzyme composition comprising at least two cellulases is already present in the one or more first containers before the lignocellulosic material is added. In another embodiment the enzyme composition comprising at least two cellulases may be added to the one or more first containers. In an embodiment the lignocellulosic material is already present in the one or more first containers before the enzyme composition comprising at least two cellulases is added. In an embodiment both the lignocellulosic material and the enzyme composition comprising at least two cellulases are added simultaneously to the one or more first containers. The enzyme composition present in the one or more first containers may be an aqueous composition.

The lignocellulosic material used in the processes of the present invention may be washed and/or pretreated.

In an embodiment additional enzymes are added after the first stage of the processes according to the present invention. The additional enzymes may be added before or during the second stage. In case the first stage comprises a separate liquefaction step and saccharification step, additional enzymes may be added during and/or after the liquefaction step. These additional enzymes may be added before and/or during the saccharification step. Additional enzymes may also be added after the saccharification step, before and/or during the second stage.

In an embodiment the first stage takes 12-200 hours, preferably 18-120 hours, more preferably 24-72 hours. In case of a process wherein liquefaction and saccharification are separate steps, the liquefaction step takes 2-24 hours, preferably 4-18 hours, more preferably 4-12 hours and/or the saccharification step takes 10-200 hours, preferably 24-120 hours, more preferably 24-72 hours.

In an embodiment the second stage takes 2-72 hours, preferably 4-48 hours, and more preferably 8-24 hours.

In an embodiment the total hydrolysis time (i.e. time of first stage and second stage) is 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more.

In an embodiment, the total hydrolysis time (i.e. time of first stage and second stage) is 14 to 272 hours, 16 to 248 hours, preferably 20 to 224 hours. Due to the stability of the enzyme composition longer hydrolysis reaction times are possible with corresponding higher sugar yields.

In case of the processes according to the present invention wherein liquefaction and saccharification are combined, the viscosity of the lignocellulosic material in the one or more first containers is kept between 10 and 1000 cP, between 10 and 900 cP, between 10 and 800 cP, between 10 and 700 cP, between 10 and 600 cP, between 10 and 500 cP, between 10 and 400 cP, between 10 and 300 cP, between 10 and 200 cP and preferably between 10 and 100 cP and/or the viscosity of the lignocellulosic material in the one or more second containers is kept between 10 and 1000 cP, between 10 and 900 cP, between 10 and 800 cP, between 10 and 700 cP, between 10 and 600 cP, between 10 and 500 cP, between 10 and 400 cP, between 10 and 300 cP, between 10 and 200 cP and preferably between 10 and 100 cP.

In case of the process according to the present invention wherein liquefaction and saccharification are separate steps, the viscosity of the lignocellulosic material in the one or more first containers is kept between 10 and 1000 cP, between 10 and 900 cP, between 10 and 800 cP, between 10 and 700 cP, between 10 and 600 cP, between 10 and 500 cP, between 10 and 400 cP, between 10 and 300 cP, between 10 and 200 cP and preferably between 10 and 100 cP and/or the viscosity of the lignocellulosic material in the one or more second containers is kept between 10 and 1000 cP, between 10 and 900 cP, between 10 and 800 cP, between 10 and 700 cP, between 10 and 600 cP, between 10 and 500 cP, between 10 and 400 cP, between 10 and 300 cP, between 10 and 200 cP and preferably between 10 and 100 cP and/or the viscosity of the lignocellulosic material in the one or more third containers is kept between 10 and 1000 cP, between 10 and 900 cP, between 10 and 800 cP, between 10 and 700 cP, between 10 and 600 cP, between 10 and 500 cP, between 10 and 400 cP, between 10 and 300 cP, between 10 and 200 cP and preferably between 10 and 100 cP.

The viscosity can be determined with a Brookfield DV III Rheometer at the temperature used for the hydrolysis.

In an embodiment oxygen is added during at least part of the second stage. Oxygen can be added continuously or discontinuously during the second stage. In an embodiment oxygen is added one or more than once during the second stage. In an embodiment oxygen may be added before hydrolysis of the second stage, during a part of hydrolysis of the second stage, during the whole hydrolysis of the second stage or any combination thereof. Oxygen is added to the one or more containers used in the second stage.

Oxygen can be added in several forms. For example, oxygen can be added as oxygen gas, oxygen-enriched gas, such as oxygen-enriched air, or air. Oxygen may also be added by means of in situ oxygen generation. For example, oxygen may be generated by electrolysis, oxygen may be produced enzymatically, e.g. by the addition of peroxide, or oxygen may be produced chemically, e.g. by an oxygen generating system such as $KHSO_5$. For example, oxygen is produced from peroxide by catalase. The peroxide can be added in the form of dissolved peroxide or generated by an enzymatic or chemical reaction. In case catalase is used as enzyme to produce oxygen, catalase present in the enzyme composition for the hydrolysis can be used or catalase can be added for this purpose.

Examples how to add oxygen include, but are not limited to, addition of oxygen by means of sparging, electrolysis, chemical addition of oxygen, filling the one or more containers used in the second stage and/or the one or more containers used for fermentation and/or the one or more containers used for propagation of the fermenting microorganisms from the top (plunging the hydrolysate into the tank and consequently introducing oxygen into the hydrolysate) and addition of oxygen to the headspace of said one or more containers. When oxygen is added to the headspace of the container(s), sufficient oxygen necessary for the hydrolysis reaction may be supplied. In general, the amount of oxygen added to the container(s) can be controlled and/or varied. Restriction of the oxygen supplied is possible by adding only oxygen during part of the hydrolysis time in said container(s). Another option is adding oxygen at a low concentration, for example by using an mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the liquid hydrolysis container contents of lignocellulosic material. It can also be blown into the headspace of the container.

In an embodiment oxygen is added to the one or more containers used in the second stage before and/or during and/or after the addition of the lignocellulosic material to said one or more containers. The oxygen may be introduced together with the lignocellulosic material that enters the hydrolysis container(s). The oxygen may be introduced into the material stream that will enter the container(s) or with part of the container(s) contents that passes an external loop of the container(s).

In an embodiment, the oxygen concentration (DO) in the lignocellulosic material present during the enzymatic hydrolysis of the second stage is at least 0.0023 mol/m$^3$, preferably at least 0.023 mol/m$^3$, more preferably at least 0.046 mol/m$^3$, even more preferably at least 0.115 mol/m$^3$, most preferably at least 0.17 mol/m$^3$ and in particular at least 0.23 mol/m$^3$. 0.23 mol/m$^3$ corresponds to 100% DO at 32° C. Temperature and pressure will influence the DO.

The preferred and exemplary mol/m$^3$ values given above relate to normal atmospheric pressure and a temperature of about 32° C. The skilled person in the art will appreciate favourable DO values on basis of the present teachings.

In the enzymatic hydrolysis amorphous and crystalline polysaccharides or cellulose are hydrolysed to sugars such as glucose. Amorphous polysaccharides are for example converted to oligosaccharides by endoglucanases and then the oligosaccharides can be converted by cellobiohydrolases and beta-glucosidases to glucose. The conversion of the crystalline polysaccharides may occur in parallel or sequential and continue even when most of the amorphous polysaccharides are hydrolysed. The addition of oxygen in combination with lytic polysaccharide monooxygenases is beneficial during the hydrolysis of the crystalline polysaccharides for example in the degradation of the polysaccharides into oligosaccharides. The crystalline glucan structure can be opened by lytic polysaccharide monooxygenases. This type of enzyme opens up the structure by oxidizing the glycosidic bonds and making it accessible for the other cellulolytic enzymes for further hydrolysing the oligosaccharides into glucose. The addition of oxygen is very useful, especially in the phase wherein crystalline polysaccharides are converted by enzymes.

The processes of the present invention show advantages, especially on pilot plant and industrial scale. In an embodiment the containers used in the processes of the present invention have a volume of at least 1 m³. Preferably, the containers have a volume of at least 1 m³, at least 2 m³, at least 3 m³, at least 4 m³, at least 5 m³, at least 6 m³, at least 7 m³, at least 8 m³, at least 9 m³, at least 10 m³, at least 15 m³, at least 20 m³, at least 25 m³, at least 30 m³, at least 35 m³, at least 40 m³, at least 45 m³, at least 50 m³, at least 60 m³, at least 70 m³, at least 75 m³, at least 80 m³, at least 90 m³, at least 100 m³, at least 200 m³, at least 300 m³, at least 400 m³, at least 500 m³, at least 600 m³, at least 700 m³, at least 800 m³, at least 900 m³, at least 1000 m³, at least 1500 m³, at least 2000 m³, at least 2500 m³. In general, the container(s) will be smaller than 3000 m³ or 5000 m³. The containers used in the processes of the present invention may have the same volume, but also may have a different volume.

In an embodiment the enzyme composition used in the processes of the present invention is derived from a fungus or the enzyme composition used in the processes of the present invention comprises a fungal enzyme. In an embodiment the enzyme composition is derived from a filamentous fungus or the enzyme composition comprises a filamentous fungal enzyme. "Filamentous fungi" include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes pleurotus, Trichoderma* and *Trichophyton*.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

The processes of the invention are advantageously applied in combination with enzyme compositions derived from a microorganism of the genus *Rasamsonia*, or the enzyme composition comprises a *Rasamsonia* enzyme.

The enzymatic hydrolysis of the first stage is preferably done at 50-90° C. In this step thermostable cellulolytic enzymes are preferred. A "thermostable" enzyme as used herein means that the enzyme has a temperature optimum of 50° C. or higher, 60° C. or higher, 70° C. or higher, 75° C. or higher, 80° C. or higher, 85° C. or higher. They may for example be isolated from thermophilic microorganisms or may be designed by the skilled person and artificially synthesized. In one embodiment the polynucleotides may be isolated or obtained from thermophilic or thermotolerant filamentous fungi or isolated from non-thermophilic or non-thermotolerant fungi, but are found to be thermostable.

By "thermophilic fungus" is meant a fungus that grows at a temperature of 50° C. or higher. By "themotolerant" fungus is meant a fungus that grows at a temperature of 45° C. or higher, having a maximum near 50° C.

Suitable thermophilic or thermotolerant fungal cells may be a *Humicola, Rhizomucor, Myceliophthora, Rasamsonia, Talaromyces, Thermomyces, Thermoascus* or *Thielavia* cell, preferably a *Rasamsonia* cell. Preferred thermophilic or thermotolerant fungi are *Humicola grisea* var. *thermoidea, Humicola lanuginosa, Myceliophthora thermophila, Papulaspora thermophilia, Rasamsonia byssochlamydoides, Rasamsonia emersonii, Rasamsonia argillacea, Rasamsonia eburnean, Rasamsonia brevistipitata, Rasamsonia cylindrospora, Rhizomucor pusillus, Rhizomucor miehei, Talaromyces bacifisporus, Talaromyces leycettanus, Talaromyces thermophilus, Thermomyces lenuginosus, Thermoascus crustaceus, Thermoascus thermophilus Thermoascus aurantiacus* and *Thielavia terrestris*.

Thermophilic fungi are not restricted to a specific taxonomic order and occur all over the fungal tree of life. Examples are *Rhizomucor* in the Mucorales, *Myceliophthora* in Sordariales and *Talaromyces, Thermomyces* and *Thermoascus* in the Eurotiales (see Mouchacca, 1997). The majority of *Talaromyces* species are mesophiles, but exceptions are species within sections *Emersonii* and *Thermophila*. Section *Emersonii* includes *Talaromyces emersonii, Talaromyces byssochlamydoides, Talaromyces bacifisporus* and *Talaromyces leycettanus*, all of which grow well at 40° C. *Talaromyces bacifisporus* is thermotolerant, *Talaromyces leycettanus* is thermotolerant to thermophilic, and *Talaromyces emersonii* and *Talaromyces byssochlamydoides* are truly thermophilic (see Stolk and Samson, 1972). The sole member of *Talaromyces* section *Thermophila, Talaromyces thermophilus*, grows rapidly at 50° C. (see Stolk and Samson, 1972). The current classification of these thermophilic *Talaromyces* species is mainly based on phenotypic and physiological characters, such as their ability to grow above 40° C., ascospore color, the structure of ascornatal covering and the formation of a certain type of anamorph. Stolk and Samson (1972) stated that the members of the section *Emersonii* have anamorphs of either *Paecilomyces* (*Talaromyces byssochlamydoides* and *Talaromyces leycettanus*) or *Penicillium cylindrosporum* series (*Talaromyces emersonii* and *Talaromyces baciffisporus*). Later, Pitt (1979) transferred the species belonging to the *Penicillium cylindrosporum* series to the genus *Geosmithia*, based on various characters such as the formation of conidia from terminal pores instead of on collula (necks), a character of *Penicillium* and *Paecilomyces*. Within the genus *Geosmithia*, only *Geosmithia argillacea* is thermotolerant, and Stolk et al. (1969) and Evans (1971) proposed a connection with members of *Talaromyces* sect. *Emersonii*. The phylogenetic relationship of the thermophilic *Talaromyces* species within *Talaromyces* and the Trichocomaceae is unknown. (see J. Houbraken, Antonie van Leeuwenhoek 2012 February; 101 (2): 403-21).

*Rasamsonia* is a new genus comprising thermotolerant and thermophilic *Talaromyces* and *Geosmithia* species (J. Houbraken et al., vida supra). Based on phenotypic, physiological and molecular data, Houbraken et al. proposed to transfer the species *Talaromyces emersonii, Talaromyces byssochlamydoides, Talaromyces eburneus, Geosmithia argillacea* and *Geosmithia cylindrospora* to *Rasamsonia* gen. nov. Preferred thermophilic fungi are *Rasamsonia byssochlamydoides, Rasamsonia emersonii, Thermomyces lenuginosus, Talaromyces thermophilus, Thermoascus crustaceus, Thermoascus thermophilus* and *Thermoascus aurantiacus*, with *Rasamsonia emersonii* being most preferred. *Talaromyces emersonii, Penicillium geosmithia emersonii* and *Rasamsonia emersonii* are used interchangeably herein.

Cellulolytic enzymes of *Rasamsonia* applied on pretreated lignocellulosic feedstock show maximal conversion rates at temperature within the range of 50 to 70° C. The enzymes remain active under these circumstances for 14 days and more without complete cessation of activity. By using optimal temperature conditions, a maximal amount of reducing sugars can be released from lignocellulosic material (total hydrolysis) within the shortest possible hydrolysis time. In this way, 100% conversion of cellulose in glucose can be achieved in less than 5 days. The theoretical maximum yield (Yps max in g product per gram glucose) of a fermentation product can be derived from textbook biochemistry. For ethanol, 1 mole of glucose (180 g) yields according to normal glycolysis fermentation pathway in yeast 2 moles of ethanol (=2×46=92 g ethanol). The theoretical maximum yield of ethanol on glucose is therefore 92/180=0.511 g ethanol/g glucose. For butanol (MW 74 g/mole) or isobutanol, the theoretical maximum yield is 1 mole of butanol per mole of glucose. So Yps max for (iso-)butanol=74/180=0.411 g (iso-)butanol/g glucose. For lactic acid the fermentation yield for homolactic fermentation is 2 moles of lactic acid (MW=90 g/mole) per mole of glucose. According to this stoichiometry, the Yps max=1 g lactic acid/g glucose. For other fermentation products a similar calculation may be made. The cost reduction achieved with applying cellulolytic enzymes of *Rasamsonia* are the result of an overall process time reduction.

Due to the high stability of the enzymes used in the processes of the present invention, it is possible to lower the enzyme dosage and extend the use of the enzyme by prolonging the hydrolysis times. For example, 0.175 mL enzyme/g lignocellulosic material dry matter results in release of approximately 90% of the theoretical maximum of reducing sugars from pretreated lignocellulosic material within 72 h. When using 0.075 mL enzyme/g lignocellulosic material dry matter, approximately 90% conversion of the theoretical maximum is achieved within 120 h. The results show that, because of the stability of the enzyme activity, lowering the enzyme dosage can be compensated by extending the hydrolysis time to obtain the same amount of reducing sugars. The cost reduction achieved by using stable cellulolytic enzymes, such as those of *Rasamsonia*, results in lower enzyme dosages that nevertheless result in similar hydrolysis conversion yields.

In a common process for converting lignocellulosic material into ethanol, process steps are preferably done under septic conditions to lower the operational costs. Contamination and growth of contaminating microorganisms can therefore occur and result in undesirable side effects, such as lactic acid, formic acid and acetic acid production, yield losses of ethanol on substrate, production of toxins and extracellular polysaccharides. These effects may affect production costs significantly. A high process temperature and/or a short process time limits the risk on contamination during hydrolysis and fermentation. Thermostable enzymes, like those of *Rasamsonia*, are capable of hydrolysing lignocellulosic material at temperatures of higher than 60° C. At these temperatures, the risk that a contaminating microorganism will cause undesired side effects is little to almost zero.

During the fermentation step, in which ethanol is produced, temperatures are typically between 30 to 38° C. and are preferably not raised because of production losses. By applying short fermentation process times, the risks and effects of contamination and/or growth of contaminants are reduced as much as possible. With stable enzymes, like those of *Rasamsonia*, a short fermentation time can be applied and thus risks of contamination and/or growth of contaminants are reduced as much as possible. The cost reduction achieved with applying thermostable cellulolytic enzymes of *Rasamsonia* in this way, results in a lower risk of process failures due to contamination.

The first step after thermal pretreatment is to cool the pretreated material to temperatures wherein the enzymes have an optimal activity. On large scale, this is typically done by adding (cooled) water, which, besides decreasing the temperature, reduces the dry matter content. By using thermostable enzymes, like those of *Rasamsonia*, cost reduction can be achieved, because (i) less cooling of the pretreated material is required since higher temperatures are allowed during hydrolysis, and (ii) less water is added, which increases the dry matter content during hydrolysis and fermentation and thus increase the ethanol production capacity (amount produced per time unit per volume) of an ethanol plant. By using thermostable enzymes, like those of *Rasamsonia*, cost reduction may also be achieved by using cooling water having a higher temperature than the water that is used in a process with non-thermostable enzyme.

At the end of the hydrolysis, enzyme activities appear to be low, since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, cantation, sedimentation, 60% or more (e.g. 70%) of the enzyme activity in solution can be recovered and re-used for hydrolysis of a new pretreated lignocellulosic material during the next hydrolysis.

Moreover, after solid-liquid separation the enzyme in solution can be separated from the solution containing reducing sugars and other hydrolysis products from the enzymatic actions. This separation can be done by techniques including, but not limited to, ultra- and microfiltration, centrifugation, cantation, sedimentation, with or without first adsorption of the enzyme to a carrier of any kind. For example, after hydrolysis of pretreated material with 0.175 mL/g material dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60 to 70%. The cost reduction achieved by using stable cellulolytic enzymes, such as those of *Rasamsonia*, in this way is the consequence of a lower enzyme dosage.

The process including enzyme recycling after hydrolysis, as described above, can be combined with recycling of the ethanol producing microorganism after fermentation and with the use of the reducing sugars containing filtrate as a substrate (purified and/or concentrated or diluted) in enzyme production fermentation and as substrate for the cultivation of the ethanol producing microorganism.

The thermostability of enzymes, like those from *Rasamsonia*, causes remaining cellulolytic activity after hydrolysis, fermentation and vacuum distillation in the thin stillage. The total activity of the enzyme is reduced during the three successive process steps. The thin stillage obtained after vacuum distillation can thus be re-used as a source of enzyme for a newly started hydrolysis-fermentation-distillation process cycle of pretreated material conversion into ethanol. The thin stillage can be used either in concentrated or (un)diluted form and/or purified and with or without additional enzyme supplementation.

In an optimal process, an amount of enzyme is supplemented into the thin stillage, before its re-use in a new process cycle, equal to the amount of activity lost during the three successive process steps of the previous process cycle. In this way over dosage of enzyme is avoided and thus most efficient use of enzyme is obtained. Moreover, by providing high enzyme dosage in the first process cycle, and supplementing enzyme equal to the amount of activity lost during the three successive process steps in the following process cycles, highest possible hydrolysis rates can be obtained in each process cycle resulting in short hydrolysis times of less than 48 h in combination with most efficient use of enzymes.

By applying mixing during hydrolysis, enzymes come more often in contact with substrates, which results in a more efficient use of the catalytic activity. This will result in a lower enzyme dosages and thus in lower costs, unless the mixing has a negative effect on the enzymes. Stable enzymes, like the thermostable enzymes from *Rasamsonia*, are robust and can resist circumstances of (locally) high shear and temperatures, which is the case during intensive mixing of slurries. The use of them in mixed systems is therefore beneficial and will lead to dosage and thus costs reduction.

An advantage of expression and production of the enzymes (for example at least two, three or four different cellulases) in a suitable microorganism may be a high enzyme composition yield which can be used in the processes of the present invention.

In the processes of the present invention enzyme compositions are used. Preferably, the compositions are stable. "Stable enzyme compositions" as used herein means that the enzyme compositions retain activity after 30 hours of hydrolysis reaction time, preferably at least 10%, 20%, 30%, 40%, 50%, 60%, 65%, 70%, 75%, 80% 85%, 90%, 95%, 96%, 97%, 98%, 99% or 100% of its initial activity after 30 hours of hydrolysis reaction time. Preferably, the enzyme composition retains activity after 40, 50, 60, 70, 80, 90 100, 150, 200, 250, 300, 350, 400, 450, 500 hours of hydrolysis reaction time.

The enzyme composition may be prepared by fermentation of a suitable substrate with a suitable microorganism, e.g. *Rasamsonia emersonii* or *Aspergillus niger*, wherein the enzyme composition is produced by the microorganism. The microorganism may be altered to improve or to make the composition. For example, the microorganism may be mutated by classical strain improvement procedures or by recombinant DNA techniques. Therefore, the microorganisms mentioned herein can be used as such to produce the composition or may be altered to increase the production or to produce an altered composition which might include heterologous enzymes, e.g. cellulases, thus enzymes that are not originally produced by that microorganism. Preferably, a fungus, more preferably a filamentous fungus is used to produce the composition. Advantageously, a thermophilic or thermotolerant microorganism is used. Optionally, a substrate is used that induces the expression of the enzymes in the enzyme composition during the production of the enzyme composition.

The enzyme composition is used to release sugars from lignocellulosic material, that comprises polysaccharides. The major polysaccharides are cellulose (glucans), hemicelluloses (xylans, heteroxylans and xyloglucans). In addition, some hemicellulose may be present as glucomannans, for example in wood-derived lignocellulosic material. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert. By sugar product is meant the enzymatic hydrolysis product of the lignocellulosic material. The sugar product comprises soluble sugars, including both monomers and multimers. Preferably, it comprises glucose. Examples of other sugars are cellobiose, xylose, arabinose, galactose, fructose, mannose, rhamnose, ribose, galacturonic acid, glucoronic acid and other hexoses and pentoses. The sugar product may be used as such or may be further processed for example recovered and/or purified.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to inter strand hydrogen bonding than the highly branched α-linked structures of starch. Thus, cellulose polymers are generally less soluble and form more tightly bound fibers than the fibers found in starch.

Enzymes that may be included in the stable enzyme composition used in the invention are described in more detail below.

Lytic polysaccharide monooxygenases, endoglucanases (EG) and exo-cellobiohydrolases (CBH) catalyze the hydrolysis of insoluble cellulose to products such as cellooligosaccharides (cellobiose as a main product), while β-glucosidases (BG) convert the oligosaccharides, mainly cellobiose and cellotriose, to glucose.

Hemicellulose is a complex polymer, and its composition often varies widely from organism to organism and from one tissue type to another. In general, a main component of hemicellulose is β-1,4-linked xylose, a five carbon sugar. However, this xylose is often branched at 0 to 3 and/or 0 to 2 atoms of xylose, and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Xylanases together with other accessory enzymes, for example α-L-arabinofuranosidases, feruloyl and acetylxylan esterases, glucuronidases, and β-xylosidases) catalyze the hydrolysis of hemicellulose.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another. The principal types of structural unit are: galacturonan (homogalacturonan), which may be substituted with methanol on the carboxyl group and acetate on O-2 and O3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

An enzyme composition for use in the processes of the current invention comprises preferably at least two activities, although typically a composition will comprise more than two activities, for example, three, four, five, six, seven, eight, nine or even more activities. Typically, an enzyme composition for use in the processes of the current invention comprises at least two cellulases. The at least two cellulases may contain the same or different activities. The enzyme composition for use in the processes of the current invention may also comprises at least one enzyme other than a cellulase. Preferably, the at least one other enzyme has an auxiliary enzyme activity, i.e. an additional activity which, either directly or indirectly leads to lignocellulose degradation. Examples of such auxiliary activities are mentioned herein and include, but are not limited to hemicellulases.

Thus, a composition for use in the processes of the current invention may comprise lytic polysaccharide monooxygenase activity, endoglucanase activity and/or cellobiohydrolase activity and/or beta-glucosidase activity. A composition for use in the invention may comprise more than one enzyme activity per activity class. For example, a composition for use in the invention may comprise two endoglucanase activities, for example, endo-1,3(1,4)-β glucanase activity and endo-β-1,4-glucanase activity.

A composition for use in the processes of the current invention may be derived from a fungus, such as a filamentous fungus such as *Rasamsonia*, such as *Rasamsonia emersonii*. In an embodiment a core set of (lignocellulose degrading) enzyme activities may be derived from *Rasamsonia emersonii*. *Rasamsonia emersonii* can provide a highly effective set of activities as demonstrated herein for the hydrolysis of lignocellulosic material. If needed, the set of activities can be supplemented with additional enzyme activities from other sources. Such additional activities may be derived from classical sources and/or produced by a genetically modified organisms.

The activities in a composition for use in the processes of the current invention may be thermostable. Herein, this means that the activity has a temperature optimum of 60° C. or higher, 70° C. or higher, 75° C. or higher, 80° C. or higher, 85° C. or higher. Activities in a composition for use in the processes of the current invention will typically not have the same temperature optima, but preferably will, nevertheless, be thermostable.

In addition, enzyme activities in a composition for use in the processes of the current invention may be able to work at low pH. For the purposes of this invention, low pH indicates a pH of 5.5 or lower, 5 or lower, 4.9 or lower, 4.8 or lower, 4.7 or lower, 4.6 or lower, 4.5 or lower, 4.4 or lower, 4.3 or lower, 4.2 or lower, 4.1 or lower, 4.0 or lower 3.9 or lower, 3.8 or lower, 3.7 or lower, 3.6 or lower, 3.5 or lower.

Activities in a composition for use in the processes of the current invention may be defined by a combination of any of the above temperature optima and pH values.

The enzyme composition for use in the processes of the current invention may comprise a cellulase and/or a hemicellulase and/or a pectinase from a source other than *Rasamsonia*.

For example, the enzyme composition for use in the processes of the current invention may comprise a beta-glucosidase (BG) from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus* or *Aspergillus kawachi*. In another embodiment the beta-glucosidase is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982, 159, 7,045,332, 7,005,289, US 2006/0258554 US 2004/0102619. In an embodiment even a bacterial beta-glucosidase can be used.

For example, the enzyme composition for use in the processes of the current invention may comprise an endoglucanase (EG) from *Trichoderma*, such as *Trichoderma reesei*; from *Humicola*, such as a strain of *Humicola insolens*; from Aspergillus, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; and/or from *Chrysosporium*, such as a strain of *Chrysosporium lucknowense*. In an embodiment even a bacterial endoglucanase can be used.

For example, the enzyme composition for use in the processes of the current invention may comprise a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812, or from *Trichoderma*, such as *Trichoderma reesei*.

For example, the enzyme composition for use in the processes of the current invention may comprise a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Thielavia*, such as *Thielavia terrestris*, such as cellobiohydrolase II CEL6A from *Thielavia terrestris*.

For example, the enzyme composition for use in the processes of the current invention may comprise a GH61 polypeptide (a lytic polysaccharide monooxygenase) from *Thermoascus*, such as *Thermoascus aurantiacus*, such as the one described in WO 2005/074656 as SEQ ID NO:2 and SEQ ID NO:1 in WO2014/130812; or from *Thielavia*, such as *Thielavia terrestris*, such as the one described in WO 2005/074647 as SEQ ID NO: 8 or SEQ ID NO:4 in WO2014/130812; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812.

An enzyme composition for use in the processes of the current invention may comprise one, two, three, four classes or more of cellulase, for example one, two, three or four or all of a lytic polysaccharide monooxygenas (LPMO), an endoglucanase (EG), one or two exo-cellobiohydrolase (CBH) and a beta-glucosidase (BG). A composition for use in the processes of the current invention may comprise two or more of any of these classes of cellulase.

An enzyme composition for use in the processes of the current invention may comprise one type of cellulase activity and/or hemicellulase activity and/or pectinase activity provided by a composition as described herein and a second type of cellulase activity and/or hemicellulase activity and/or pectinase activity provided by an additional cellulase/hemicellulase/pectinase.

As used herein, a cellulase is any polypeptide which is capable of degrading or modifying cellulose. A polypeptide which is capable of degrading cellulose is one which is capable of catalyzing the process of breaking down cellulose into smaller units, either partially, for example into cellodextrins, or completely into glucose monomers. A cellulase according to the invention may give rise to a mixed population of cellodextrins and glucose monomers. Such degradation will typically take place by way of a hydrolysis reaction.

Lytic polysaccharide monooxygenases (LPMO) are recently classified by CAZy in family AA9 (Auxiliary Activity Family 9) or family AA10 (Auxiliary Activity Family 10). As mentioned above, lytic polysaccharide monooxygenases are able to open a crystalline glucan structure. Lytic polysaccharide monooxygenases may also affect cello-oligosaccharides. GH61 (glycoside hydrolase family 61 or sometimes referred to EGIV) proteins are (lytic) oxygen-dependent polysaccharide monooxygenases (PMO's/LPMO's) according to the latest literature (see Isaksen et al., Journal of Biological Chemistry, vol. 289, no. 5, pp. 2632-2642). PMO and LPMO are used herein interchangeably. Often in literature these proteins are mentioned to enhance the action of cellulases on lignocellulose substrates. GH61 was originally classified as endoglucanase based on measurement of very weak endo-1,4-β-d-glucanase activity in one family member. The term "GH61" as used herein, is to be understood as a family of enzymes, which share common conserved sequence portions and folding to be classified in family 61 of the well-established CAZy GH classification system (www.cazy.org/GH61.html). The glycoside hydrolase family 61 is a member of the family of glycoside hydrolases EC 3.2.1. GH61 are recently now reclassified by CAZy in family AA9 (Auxiliary Activity Family 9). GH61 is used herein as being part of the cellulases.

CBM33 (family 33 carbohydrate-binding module) is a lytic polysaccharide monooxygenase (see Isaksen et al, Journal of Biological Chemistry, vol. 289, no. 5, pp. 2632-2642), CAZy has recently reclassified CBM33 in AA10 (Auxiliary Activity Family 10).

As used herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalyzing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers. Such degradation will typically take place by way of a hydrolysis reaction.

As used herein, a pectinase is any polypeptide which is capable of degrading or modifying pectin. A polypeptide which is capable of degrading pectin is one which is capable of catalyzing the process of breaking down pectin into smaller units, either partially, for example into oligosaccharides, or completely into sugar monomers. A pectinase according to the invention may give rise to a mixed population of oligosacchardies and sugar monomers. Such degradation will typically take place by way of a hydrolysis reaction.

Accordingly, an enzyme composition for use in the processes of the current invention may comprise any cellulase, for example, a lytic polysaccharide monooxygenase (e.g. GH61), a cellobiohydrolase, an endo-β-1,4-glucanase, a beta-glucosidaseor a β-(1,3)(1,4)-glucanase.

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

As used herein, an endo-β-1,4-glucanase (EC 3.2.1.4) is any polypeptide which is capable of catalyzing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase. Substrates include laminarin, lichenin and cereal beta-D-glucans.

A composition for use in the processes of the current invention may comprise any hemicellulase, for example, an endoxylanase, a β-xylosidase, a α-L-arabinofuranosidase, an α-D-glucuronidase, an acetyl xylan esterase, a feruloyl esterase, a coumaroyl esterase, an α-galactosidase, a β-galactosidase, a β-mannanase or a β-mannosidase.

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

As used herein, a β-xylosidase (EC 3.2.1.37) is any polypeptide which is capable of catalysing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

As used herein, a feruloyl esterase (EC 3.1.1.73) is any polypeptide which is capable of catalysing a reaction of the form: feruloyl-saccharide+$H_2O$=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

A composition for use in the processes of the current invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction:

pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: (1,4-α-D-galacturonide)$_n$+H$_2$O=(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

An enzyme composition for use in the processes of the current invention will typically comprise at least two cellulases and optionally at least one hemicellulase and optionally at least one pectinase. A composition for use in the processes of the current invention may comprise a lytic polysaccharide monooxygenases (such as GH61), a cellobiohydrolase, an endoglucanase and/or a beta-glucosidase. Such a composition may also comprise one or more hemicellulases and/or one or more pectinases.

In addition, one or more (for example two, three, four or all) of an amylase, a protease, a lipase, a ligninase, a hexosyltransferase, a glucuronidase, an expansin, a cellulose induced protein or a cellulose integrating protein or like protein may be present in a composition for use in the processes of the current invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes of the current invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition for use in the processes of the current invention may comprise an expansin or expansin-like protein, such as a swollenin (see Salheimo et al., Eur. J. Biochem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition for use in the processes of the current invention may comprise a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multifunctional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition for use in the processes of the current invention may also comprise a catalase. The term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

A composition for use in the processes of the current invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition for use in the processes of the current invention may be composed of enzymes from (1) commercial suppliers; (2) cloned genes expressing enzymes; (3) broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic material. Alternatively, the enzyme may be produced in a fermentation that uses (pretreated) lignocellulosic material (such as corn stover or wheat straw) to provide nutrition to an organism that produces an enzyme(s). In this manner, plants that produce the enzymes may themselves serve as a lignocellulosic material and be added into lignocellulosic material.

In the uses and methods described herein, the components of the compositions described above may be provided concomitantly (i.e. as a single composition per se) or separately or sequentially.

In an embodiment the enzyme compositions may be a whole fermentation broth as described below. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus wherein the one or more genes encode enzymes that can degrade a cellulosic substrate. The whole fermentation broth may comprise any of the polypeptides or any combination thereof.

Preferably, the enzyme composition is whole fermentation broth wherein the cells are killed. The whole fermentation broth may contain organic acid(s) (used for killing the cells), killed cells and/or cell debris, and culture medium.

Generally, the filamentous fungi is cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express the one or more cellulases and/or hemicellulases and/or pectinases. Once enzymes, such as cellulases and/or hemicellulases and/or pectinases, are secreted by the filamentous fungi into the fermentation medium, the whole fermentation broth can be used. The whole fermentation broth of the present invention may comprise filamentous fungi. In some embodiments, the whole fermentation broth comprises the unfractionated contents of the fermentation materials derived at the end of the fermentation. Typically, the whole fermentation broth comprises the spent culture medium and cell debris present after the filamentous fungi is grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. In some embodiments, the filamentous fungi present in whole fermentation broth can be lysed, permeabilized, or killed using methods known in the art to produce a cell-killed whole fermentation broth. In an embodiment, the whole fermentation broth is a cell-killed whole fermentation broth, wherein the whole fermentation broth containing the filamentous fungi cells are lysed or killed. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably non-viable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or anti-microbial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth and the enzymes may be a component of a separate whole fermentation broth, or may be purified, or minimally recovered and/or purified.

In an embodiment, the whole fermentation broth comprises a whole fermentation broth of a fermentation of a recombinant filamentous fungi overexpressing one or more enzymes to improve the degradation of the cellulosic substrate. Alternatively, the whole fermentation broth can comprise a mixture of a whole fermentation broth of a fermentation of a non-recombinant filamentous fungus and a recombinant filamentous fungus overexpressing one or more enzymes to improve the degradation of the cellulosic substrate. In an embodiment, the whole fermentation broth comprises a whole fermentation broth of a fermentation of a filamentous fungi overexpressing beta-glucosidase. Alternatively, the whole fermentation broth for use in the present methods and reactive compositions can comprise a mixture of a whole fermentation broth of a fermentation of a non-recombinant filamentous fungus and a whole fermentation broth of a fermentation of a recombinant filamentous fungi overexpressing a beta-glucosidase.

As described above, an enzyme composition is present in the first stage and in the second stage of the processes of the current invention. These enzyme compositions may be the same or may be different. Furthermore, as described above, additional enzymes are added during the first stage and/or the second stage of the processes according to the present invention. The enzymes added may be enzymes that are already present in the first stage and in the second stage. Alternatively, they may be different enzymes. Moreover, the additional enzymes added during the first stage may differ or may be the same as the additional enzymes added during the second stage of the processes according to the present invention.

Lignocellulosic material as used herein includes any lignocellulosic and/or hemicellulosic material. Lignocellulosic material suitable for use in the processes of the current invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane, cane straw, sugar cane bagasse, switch grass, miscanthus, energy cane, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

Cellulose is an organic compound with the formula $(C_6H_{10}O_5)_n$, a polysaccharide consisting of a linear chain of several hundred to over ten thousand β(1→4) linked D-glucose units. A glucan molecule is a polysaccharide of D-glucose monomers linked by glycosidic bonds. Herein glucan and cellulose are used interchangeably for a polysaccharide of D-glucose monomers linked by glycosidic bonds. Methods for the quantitative analysis of glucan or polysaccharide compositions are well-known and described in the art and are for example summarized in Carvalho de Souza et al., Carbohydrate Polymers 95 (2013) 657-663. In general, 50 to 70% of the glucan is crystalline cellulose, the remainder is amorphous cellulose.

In an embodiment the lignocellulosic material is pretreated before and/or during the enzymatic hydrolysis. Pretreatment methods are known in the art and include, but are not limited to, heat, mechanical, chemical modification, biological modification and any combination thereof. Pretreatment is typically performed in order to enhance the accessibility of the lignocellulosic material to enzymatic hydrolysis and/or hydrolyse the hemicellulose and/or solubilize the hemicellulose and/or cellulose and/or lignin, in the lignocellulosic material. In an embodiment, the pretreatment comprises treating the lignocellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

The lignocellulosic material may be washed. In an embodiment the lignocellulosic material may be washed after the pretreatment. The washing step may be used to remove water soluble compounds that may act as inhibitors for the fermentation and/or hydrolysis step. The washing step may be conducted in manner known to the skilled person. Next to washing, other detoxification methods do exist. The pretreated lignocellulosic material may also be detoxified by any (or any combination) of these methods which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

The enzyme composition used in the process of the invention can extremely effectively hydrolyze lignocellulosic material, for example corn stover, wheat straw, cane straw, and/or sugar cane bagasse, which can then be further converted into a product, such as ethanol, biogas, butanol, a plastic, an organic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials. The present invention is exemplified with the production of ethanol but this is done as exemplification only rather than as limitation, the other products mentioned can be produced equally well.

In an embodiment the amount of enzyme composition added (herein also called enzyme dosage or enzyme load) in the first stage is low. In an embodiment the amount of enzyme is 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). A low enzyme dosage is possible, because of the activity and stability of the enzymes. In case, also enzyme composition is added in the second stage, the amount of enzyme composition added in the enzymatic hydrolysis in the first stage and/or the second stage may differ or may be the same.

The pH during the enzymatic hydrolysis of the first stage and/or the second stage may be chosen by the skilled person. In an embodiment the pH during the hydrolysis may be 3.0 to 6.4. The stable enzymes of the invention may have a broad pH range of up to 2 pH units, up to 3 pH units, up to 5 pH units. The optimum pH may lie within the limits of pH 2.0 to 8.0, 2.5 to 7.5, 3.0 to 7.0, 3.5 to 6.5, 4.0 to 5.0, 4.0 to 4.5 or is about 4.2. The pH used in the enzymatic hydrolysis of the first stage and the second stage may differ or may be the same. The optimum pH of the enzyme composition used in the enzymatic hydrolysis of the first stage and the second stage may differ or may be the same.

In an embodiment the hydrolysis step is conducted until 70% or more, 80% or more, 85% or more, 90% or more, 92% or more, 95% or more of available sugar in the lignocellulosic material is released.

Significantly, a process of the invention may be carried out using high levels of dry matter (of the lignocellulosic material) in the hydrolysis reaction. In an embodiment the dry matter content at the end of the enzymatic hydrolysis of the first stage is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the enzymatic hydrolysis of the first stage is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the enzymatic hydrolysis of the second stage is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the enzymatic hydrolysis of the second stage is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the fermentation of the processes according to the present invention is performed in one or more containers. The fermentation can be done in the same container(s) wherein the enzymatic hydrolysis of the second stage is performed. Alternatively, the fermentation can be performed in one or more separate containers. In a further aspect, the invention thus includes fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic material (e.g. 50 g/l xylose, 35 g/l L-arabinose and 10 g/l galactose). For more dilute sugar compositions, the fermentation time may correspondingly be reduced.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C.

In an embodiment of the invention, the fermentation is conducted with a fermenting microorganism. In an embodiment the fermentation is performed in one or more containers. In an embodiment the second stage is performed in the one or more fermentation containers. In an embodiment the second stage is performed before the fermenting microorganism is added to the one or more fermentation containers.

In an embodiment the second stage is performed together with the propagation step of the fermenting microorganism. This means that the second stage is performed in one or more containers used for the propagation of the fermenting microorgansims.

In an embodiment the fermenting microorganism is a microorganism that is able to ferment at least one C5 sugar. In an embodiment the process is a process for the production of ethanol, wherein the process comprises the step of fermenting a medium containing sugar(s) with a microorganism that is able to ferment at least one C5 sugar. The microorganism may be a prokaryotic or eukaryotic organism. The microorganism used in the process may be a genetically engineered microorganism. Examples of suitable organisms are yeasts, for instance *Saccharomyces*, e.g. *Saccharomyces cerevisiae, Saccharomyces pastorianus* or *Saccharomyces uvarum, Hansenula, Issatchenkia*, e.g. *Issatchenkia orientalis, Pichia*, e.g. *Pichia stipites* or *Pichia pastoris, Kluyveromyces*, e.g. *Kluyveromyces fagilis, Candida*, e.g. *Candida pseudotropicalis* or *Candida acidothermophilum, Pachysolen*, e.g. *Pachysolen tannophilus* or bacteria, for instance *Lactobacillus*, e.g. *Lactobacillus lactis, Geobacillus, Zymomonas*, e.g. *Zymomonas mobilis, Clostridium*, e.g. *Clostridium phytofermentans, Escherichia*, e.g. *E. coli, Klebsiella*, e.g. *Klebsiella oxytoca*. In an embodiment the microorganism that is able to ferment at least one C5 sugar is a yeast. In an embodiment, the yeast is belongs to the genus *Saccharomyces*, preferably of the species *Saccharomyces cerevisiae*. The yeast, e.g. *Saccharomyces cerevisiae*, used in the processes according to the present invention is capable of converting hexose (C6) sugars and pentose (C5) sugars. The yeast, e.g. *Saccharomyces cerevisiae*, used in the processes according to the present invention can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TAL1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

The volumetric ethanol productivity is preferably at least 0.5, 1.0, 1.5, 2.0, 2.5, 3.0, 5.0 or 10.0 g ethanol per liter per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g ethanol per g glucose or xylose.

In one aspect, the fermentation process leading to the production of ethanol, has several advantages by comparison to known ethanol fermentations processes: anaerobic processes are possible; oxygen limited conditions are possible; higher ethanol yields and ethanol production rates can be obtained; the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The fermentation process may be carried out without any requirement to adjust the pH during the process. That is to say, the process is one which may be carried out without the addition of any acid(s) or base(s). However, this excludes a pretreatment step, where acid may be added. The point is that the enzyme composition used in the processes of the invention is capable of acting at low pH and, therefore, there is no need to adjust the pH of acid of an acid pretreated feedstock in order that hydrolysis may take place. Accordingly, the processes of the invention may be zero waste processes using only organic products with no requirement for inorganic chemical input.

The overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly, lower overall reaction times may be reached at lower glucose yield.

Fermentation products that may be produced by the processes of the invention can be any substance derived from fermentation, They include, but are not limited to, alcohols (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase.

The processes according to the invention optionally comprise recovery of fermentation product. A fermentation product may be separated from the fermentation broth in manner know to the skilled person. For each fermentation product the skilled person will thus be able to select a proper separation technique. For instance, ethanol may be separated from a yeast fermentation broth by distillation, for instance steam distillation/vacuum distillation in conventional way.

The beneficial effects of the present invention are found for several lignocellulosic materials and therefore believed to be present for the hydrolysis of all kind of lignocellulosic materials. This beneficial effects of the present invention are found for several enzyme compositions and therefore believed to be present for all kind of hydrolysing enzyme compositions.

EXAMPLES

Example 1

The Effect of Oxygen Addition and Reduced Temperature on Glucose Production and Ethanol Production The following experiment is conducted to demonstrate the effect of oxygen at reduced temperature during enzymatic hydrolysis. Two stirred tank reactors are filled with 1 kg of 20% w/w acid pretreated corn stover feedstock. The pH is adjusted to pH 4.5 using 10% w/w ammonia and the temperature is set at 62° C. The obtained mixture is stirred at 60 rpm using a marine impeller. 2.5 mg per gram of dry matter of a cellulase enzyme cocktail comprising lytic polysaccharide monooxygenase activity (GH61 enzyme activity) is added to the mixture and the obtained mixture is incubated for 120 hours.

The dissolved oxygen (DO) level is measured during the entire hydrolysis at 62° C. The DO level during the hydrolysis is constantly 0%, suggesting near anaerobic conditions. Gluconic acid formation is measured in hydrolysis samples. The amount of gluconic acid is 0.2 g/l in the supernatant of the hydrolysis samples taken from the mixture during the hydrolysis. Gluconic acid levels do not increase during hydrolysis, suggesting no GH61 enzyme activity during hydrolysis.

Next, the temperature is decreased to 32° C. One reactor (experiment A) is further incubated for 24 hours at a stirring speed of 60 rpm. The DO in this reactor remains at 0% DO. The other reactor (experiment B) is incubated for 24 hours at a stirring speed of 250 rpm and a constant refreshment of the head space in the reactor with fresh air at a flow rate of 100 ml/min. The DO in this reactor is about 100% during this period. Gluconic acid analysis reveals that the gluconic acid concentration increases in experiment B, while it remains constant in experiment A. This suggests GH61 enzyme activity in experiment B and not in experiment A.

Next, the pH is adjusted to pH 5.5 using 10% w/w ammonia and 0.5 g/kg hydrolysate of yeast is added to start the fermentation. The fermentation is performed for 72 hours, while the pH is not controlled during fermentation. The resulting glucose formation is shown in Table 1.

Table 1 demonstrates a substantial increase in glucose production in case of a second stage enzymatic hydrolysis wherein the temperature is lowered (to 32° C.) compared to the first stage hydrolysis and wherein aeration is applied during the second stage.

The amount of ethanol produced in experiment B (with aeration) is about 20% higher compared to experiment A (without aeration).

Example 2

The Effect of Hydrolysis Time, Oxygen Addition and Reduced Temperature on Glucose Production and Ethanol Production The following experiment is conducted to demonstrate the effect of oxygen at reduced temperature during enzymatic hydrolysis. Two stirred tank reactors are filled with 1 kg of 20% w/w acid pretreated corn stover feedstock. The pH is adjusted to pH 4.5 using 10% w/w ammonia and the temperature is set at 62° C. The reaction mixture is stirred at 60 rpm using a marine impeller. 2.5 mg per gram of dry matter of a cellulase enzyme cocktail comprising lytic polysaccharide monooxygenase activity (GH61 enzyme activity) is added to the mixture and the obtained mixture is incubated for 120 hours in experiment A and 48 hours in experiment B.

The dissolved oxygen (DO) level is measured during the entire hydrolysis at 62° C. The DO level during the hydrolysis is constantly 0%, suggesting near anaerobic conditions. Gluconic acid formation is measured in hydrolysis samples. The amount of gluconic acid is 0.2 g/l in the supernatant of the hydrolysis samples taken from the mixture during the hydrolysis. Gluconic acid levels do not increase during hydrolysis, suggesting no GH61 enzyme activity during hydrolysis.

Next, the temperature is decreased to 32° C. Both reactors are further incubated for 24 hours at a stirring speed of 250 rpm and a constant refreshment of the head space in the reactor with fresh air at a flow rate of 100 ml/min. The DO in the reactors is about 100% during this period. Gluconic acid analysis reveals that the gluconic acid concentration increases in both experiment, suggesting GH61 enzyme activity in both experiments.

Next, the pH is adjusted to pH 5.5 using 10% w/w ammonia and 0.5 g/kg hydrolysate of yeast is added to start the fermentation. The fermentation is performed for 72 hours, while the pH is not controlled during fermentation. The resulting glucose formation is shown in Table 2.

Table 2 demonstrates for short and long hydrolysis times a substantial increase in glucose production in case of a second stage enzymatic hydrolysis wherein the temperature is lowered (to 32° C.) compared to the first stage and wherein aeration is applied during the second stage.

The amount of ethanol produced in experiment A (long hydrolysis time) is the same compared to experiment A (short hydrolysis time). This suggests that the experiment having the short hydrolysis time catches up during fermentation which suggests additional monosaccharide formation during fermentation.

Example 3

Less Enzyme Inactivation of Lower Hydrolysis Temperature

The effect of hydrolysis temperature on enzyme inactivation during the hydrolysis of a 20 wt % dry matter high acid pretreated corn stover feedstock by a cellulase mixture (2.7 mg/g dry matter) was evaluated. For this purpose, hydrolysis experiments were performed at 54° C. and 62° C. in two separate stirred tank reactors filled with a 1 kg of the 20 wt % dry matter high acid pretreated corn stover feedstock. The headspace of the reactions was constantly flushed with a flow of nitrogen gas of 100 ml/min. Both reactions were stirred at 100 rpm using a marine impeller and the pH was controlled at pH 4.5 via the addition of a 10% w/w ammonia solution. After 7 hours and 120 hours representative hydrolysate samples (thus including insolubles) were taken from both reactions. Subsequently, these samples were diluted thousand-fold and beta-glucosidase activity was determined in a routine assay.

In this assay, 0.4 ml of the diluted hydrolysate sample was added to 0.4 ml of a substrate solution containing 6 mM 4-nitrophenyl-β-D-glucopyranoside in 100 mM sodium acetate buffer pH 4.5. After an incubation of 15 minutes at 60° C., the reaction was stopped via the addition of 0.8 ml of a 1M sodium carbonate solution and the absorbance was determined at a wavelength of 405 nm. The betaglucosidase activity was calculated using the molar extinction coefficient of para-nitrophenol.

Table 3 lists the beta-glucosidase activity present at the end of hydrolysis (t=120 hours) as percentage of the activity determined after 7 hours of hydrolysis for both temperatures. After 7 hours of hydrolysis, no significant difference in beta-glucosidase activity was detected between the hydrolysates operated at the two different temperatures. The data in Table 3 clearly show that there is much less beta-glucosidase inactivation in the low temperature hydrolysate. Thus hydrolysis temperature plays an important role in the inactivation of cellulase enzymes and at lower temperature, less inactivation is observed.

Example 4

Oxygen Dependent Enzyme Inactivation is Less at Lower Hydrolysis Temperature

In another experiment, the effect of oxygen on enzyme inactivation during hydrolysis was evaluated. For this purpose, four hydrolysis experiments were performed at two different temperatures (54° C. and 62° C.) and for both temperatures under aerobic and anaerobic conditions. The hydrolysis reactions were performed in four stirred tank reactors filled with 1 kg of a 20 wt % dry matter high acid pretreated corn stover feedstock using 2.7 mg/g dry matter of a cellulase mixture. The headspace of the anaerobic, oxygen-free reaction was constantly flushed with a flow of nitrogen gas of 100 ml/min, whereas the other hydrolysate headspace was continuously flushed with normal air containing oxygen (100 ml/min). All reactions were stirred at 100 rpm using a marine impeller and the pH was controlled at pH 4.5 via the addition of a 10% w/w ammonia solution. After 7 hours and 120 hours representative hydrolysate samples (thus including insolubles) were taken from both reactions. Subsequently, these samples were diluted thousand-fold and endoglucanase activity was determined in a routine assay. In this assay, 0.2 ml of the diluted hydrolysate sample was added to 0.2 ml of a substrate solution containing 2 wt % dry matter AZO-CM-cellulose (Megazyme) in 100 mM sodium acetate buffer pH 4.5. After an incubation of 10 minutes at 60° C., the reaction was stopped via the addition of 1 ml of a stop solution. This stop solution was made by dissolving 40 g of sodium acetate and 4 g of zinc acetate in 200 ml water pH 5 (adjusted with HCl) and mixing this with 800 ml 95% ethanol. After stop solution addition, the samples were vigorously vortexed for 10 seconds and centrifuged for 10 minutes at 1000×g. The supernatant was transferred to a cuvette and the absorbance at 590 nm was measured together with the blanks (same procedure only without enzyme addition) and used to determine endoglucanase activity (in mAU/mg·sec).

Table 4 lists the endoglucanase activity present at the end of hydrolysis (t=120 hours) as percentage of the activity determined after 7 hours of hydrolysis for all four conditions. No significant difference in endoglucanase activity was detected between the 7 hour samples of the four hydrolysates.

The data in Table 4 show that there is more endoglucanase inactivation in the aerobic hydrolysis samples, suggesting a relation between oxygen and enzyme inactivation. Furthermore the data show that this oxygen-dependent inactivation (calculated as the delta ($\Delta$) between the $N_2$ and $O_2$ hydrolysis reactions) is less at lower temperature.

Example 5

The Effect of Lowering the Temperature During Aerated Enzymatic Hydrolysis of Acid Pretreated Corn Stover This example demonstrates the effect of lowering the temperature during enzymatic hydrolysis of pretreated corn stover under aeration.

The hydrolysis reactions were performed with acid pretreated corn stover at a final concentration of 17.1% dry matter (w/w). The acid pretreated corn stover was prepared via dilution of a concentrated acid pretreated corn stover solution with water. Subsequently, the pH was adjusted to pH 4.5 with a 10% (w/w) $NH_4OH$ solution. The enzymatic hydrolysis was conducted for 120 hours in a stirred (250 rpm), pH-controlled and temperature-controlled reactor with a working volume of 1 l. The hydrolysis was performed with 3.75 mg TEC-210 cellulase enzyme cocktail per g of dry matter. The TEC-210 cellulase enzyme cocktail was produced according to the inoculation and fermentation procedures described in WO 2011/000949.

The following experiments were conducted:
1. The enzymatic hydrolysis was conducted in two stages. A first stage wherein the enzymatic hydrolysis was conducted at a temperature 62° C. for the first 48 hours under nitrogen (to exclude oxygen from the reaction; dissolved oxygen in the reaction mixture was 0 during the first stage). This was followed by a second stage wherein the enzymatic hydrolysis was conducted for a period of 72 hours at a temperature of 48° C. under oxygen (fresh air was added at a refreshment speed 0.1 vvm; dissolved oxygen in the reaction mixture was 100% during the second stage).
2. The enzymatic hydrolysis was conducted in two stages. A first stage wherein the enzymatic hydrolysis was conducted at a temperature 62° for the first 48 hours under nitrogen (to exclude oxygen from the reaction; dissolved oxygen in the reaction mixture was 0 during the first stage). This was followed by a second stage wherein the enzymatic hydrolysis was conducted for a period of 72 hours at a temperature of 62° under oxygen (fresh air was added at a refreshment speed 0.1 vvm; dissolved oxygen in the reaction mixture was 100% during the second stage).

At the end of the hydrolysis samples were taken, cooled on ice, centrifuged and immediately 50 μl of each supernatant was diluted with 1450 μl water. The diluted supernatant was subsequently filtered (0.45 μm filter, Pall PN 454) and the filtrates were analysed for sugar content as described below.

The sugar concentrations of the diluted samples were measured using an HPLC equipped with an Aminex HPX-87P column (Biorad #1250098) by elution with water at 85° C. at a flow rate of 0.6 ml per minute and quantified by integration of the glucose signals from refractive index detection (R.I.) calibrated with glucose standard solutions.

The results are presented in Table 5. The results clearly show that more glucose is formed in case the enzymatic hydrolysis is conducted in two stages and in the second stage the enzymatic hydrolysis is performed under aeration and at a temperature that is lower than the temperature of the first stage of the enzymatic hydrolysis compared to when the enzymatic hydrolysis is conducted in two stages and in the second stage the enzymatic hydrolysis is performed under aeration and at a temperature that is not lower than the temperature of the first stage of the enzymatic hydrolysis.

TABLE 1

Glucose formation in presence and absence of aeration at high and low temperature.

| Experiment | | Glucose formation (g/l) |
|---|---|---|
| A (without aeration at low T) | At end of 62° C. period | 48 |
| | At end of 32° C. period | 50 |
| B (with aeration at low T) | At end of 62° C. period | 48 |
| | At end of 32° C. period | 62 |

TABLE 2

Glucose formation in presence of aeration at low temperature during various hydrolysis times.

| Experiment | | Glucose formation (g/l) |
|---|---|---|
| A (120 h hydrolysis at 62° C. + 24 h hydrolysis at 32° C. and aeration) | At end of 62° C. period | 48 |
| | At end of 32° C. period | 62 |
| B (48 h hydrolysis at 62° C. + 24 h hydrolysis at 32° C. and aeration) | At end of 62° C. period | 38 |
| | At end of 32° C. period | 53 |

TABLE 3

Relative beta-glucosidase activity in hydrolysate samples.

| Hydrolysis temperature | 7 hr sample | 120 hr sample |
|---|---|---|
| 54° C. | 100% | 69% |
| 62° C. | 100% | 33% |

TABLE 4

Relative endoglucanase activity in four hydrolysate samples.

| Hydrolysis condition | | 7 hr sample | 120 hr sample | Δ ($N_2$-$O_2$) |
|---|---|---|---|---|
| 54° C. | $N_2$ | 100% | 82% | 15% |
| | Air ($O_2$) | 100% | 67% | |
| 62° C. | $N_2$ | 100% | 67% | 40% |
| | Air ($O_2$) | 100% | 27% | |

TABLE 5

Glucose formation in a two-stage enzymatic hydrolysis process.

| Experiment | Temperature during first stage of enzymatic hydrolysis (absence of $O_2$; 48 hours) | Temperature during second stage of enzymatic hydrolysis (presence of $O_2$; 72 hours) | Glucose* (in g/l) |
|---|---|---|---|
| 1 | 62° C. | 48° C. | 49.2 |
| 2 | 62° C. | 62° C. | 45.9 |

*glucose formation at the end of the enzymatic hydrolysis

The invention claimed is:

1. A process for preparation of a fermentation product from lignocellulosic material, comprising:
   enzymatic hydrolysis of the lignocellulosic material using an enzyme composition comprising at least two cellulases to obtain a sugar product, wherein the enzymatic hydrolysis comprises at least:
   a) a first stage wherein the enzymatic hydrolysis is performed at a first temperature, in one or more first container,
   b) a second stage wherein the enzymatic hydrolysis is performed at a second temperature, in one or more second container, wherein the second temperature is lower than the first temperature and wherein oxygen is added to the hydrolysis during at least part of the second stage, wherein the oxygen concentration (DO) in the lignocellulosic material present during the enzymatic hydrolysis of said second stage is at least 0.0023 mol/m$^3$ when measured at atmospheric pressure and about 32° C., and
   c) a fermentation, wherein said sugar product obtained is fermented to said fermentation product, in one or more third container, and optionally recovering the fermentation product.

2. The process according to claim 1, wherein the first temperature is from 50-90° C.

3. The process according to claim 1, wherein the second temperature is from 20-49° C.

4. The process according to claim 1, wherein the first stage takes 12-200 hours.

5. The process according to claim 1, wherein the second stage takes 2-72 hours.

6. The process according to claim 1, wherein the enzyme composition is derived from a fungus and/or a fungal enzyme composition the enzyme composition comprises a fungal enzyme.

7. The process according to claim 1, wherein the one or more first container and/or one or more second container have a volume of at least 1 m$^3$.

8. The process according to claim 6, wherein oxygen is added to the headspace of the one or more second container.

9. The process according to claim 1, wherein the dry matter content at the end of the first stage is 5 wt % or higher.

10. The process according to claim 1, wherein the dry matter content at the end of the second stage is 5 wt % or higher.

11. The process according to claim 1, wherein the enzyme composition is a whole fermentation broth.

12. The process according to claim 1, wherein the fermentation is conducted with a microorganism that is able to ferment at least one C5 sugar.

13. The process according to claim 1, wherein the lignocellulosic material is pretreated before and/or during the enzymatic hydrolysis.

14. The process according to claim 1, wherein the fermentation product is ethanol.

15. The process according to claim 1, wherein the one or more first container and/or one or more second container have a volume of at least 10 m$^3$.

16. The process of claim 1, wherein the oxygen is added by sparging.

* * * * *